US009846167B2

(12) United States Patent
Leong et al.

(10) Patent No.: US 9,846,167 B2
(45) Date of Patent: Dec. 19, 2017

(54) METHOD FOR DETECTING AND MONITORING BONE LOSS

(71) Applicant: Lawson Health Research Institute, London (CA)

(72) Inventors: Hon Sing Leong, London (CA); Leonard Luyt, London (CA); Colleen Nicole Biggs, London (CA); Andre St. Amant, London (CA); John D. Lewis, Edmonton (CA); Leonard Minuk, London (CA)

(73) Assignee: Lawson Health Research Institute, London (CA)

(*) Notice: Subject to any disclaimer, the term of this patent is extended or adjusted under 35 U.S.C. 154(b) by 0 days.

(21) Appl. No.: 14/780,210

(22) PCT Filed: Mar. 26, 2014

(86) PCT No.: PCT/CA2014/050312
§ 371 (c)(1),
(2) Date: Sep. 25, 2015

(87) PCT Pub. No.: WO2014/153661
PCT Pub. Date: Oct. 2, 2014

(65) Prior Publication Data
US 2016/0041190 A1 Feb. 11, 2016

Related U.S. Application Data

(60) Provisional application No. 61/805,471, filed on Mar. 26, 2013.

(51) Int. Cl.
*G01N 33/84* (2006.01)
*C09B 11/08* (2006.01)
*C09B 23/08* (2006.01)
*G01N 33/58* (2006.01)

(52) U.S. Cl.
CPC ............ *G01N 33/84* (2013.01); *C09B 11/08* (2013.01); *C09B 23/083* (2013.01); *G01N 33/582* (2013.01); *G01N 2800/108* (2013.01); *G01N 2800/52* (2013.01); *G01N 2800/56* (2013.01)

(58) Field of Classification Search
CPC ............. G01N 33/84; G01N 33/582; G01N 2800/108; G01N 2800/52; C09B 23/083; C09B 11/08
See application file for complete search history.

(56) References Cited

U.S. PATENT DOCUMENTS 7,374,746 B2 * 5/2008 Frangioni .......... A61K 49/0032
424/9.6

FOREIGN PATENT DOCUMENTS

WO WO02/38190 A2 5/2002

OTHER PUBLICATIONS

Kowada et al. In vivo fluorescence imaging of bone-resorbing osteoclast. J. Am. Chem. Soc. 2011, vol. 133, pp. 17772-17776.*
Palma et al. 99mTc(CO)3-labeled pamidronate and alendronate for bone imaging. Dalton Trans. 2011, vol. 40, pp. 2787-2796.*
Abildgaard et al., "Comparison of five biochemical markers of bone resorption in multiple myeloma: elevated pre-treatment levels of S-ICTP and U-Ntx are predictive for early progression of the bone disease during standard chemotherapy", British Journal of Haematology, 2003, 120, pp. 235-242.
Avolio et al., "Use of the plasma CTX for assessing the bone activity of the mandible among osteopenic and osteoporotic patients", Braz Oral Res., 2010, 24(2), pp. 250-255.
Baim and Miller, "Assessing the Clinical Utility of Serum CTX in Postmenopausal Osteoporosis and Its Use in Predicting Risk of Osteonecrosis of the Jaw", Journal of Bone and Mineral Research, 2009, 24, pp. 561-574.
Coleman, "Metastatic bone disease: clinical features, pathophysiology and treatment strategies", Cancer Treatment Reviews, 2001, 27, pp. 165-176.
Dimopoulos et al., "International myeloma working group consensus statement and guidelines regarding the current role of imaging techniques in the diagnosis and monitoring of multiple Myeloma", Leukemia, 2009, 23, pp. 1545-1556.
Fleisher et al., "Predicting risk for bisphosphonate-related osteonecrosis of the jaws: CTX versus radiographic markers", Oral Surg Oral Med Oral Pathol Oral Radiol Endod, 2010, 110, pp. 509-516.
Fujisaki et al., "Physicochemical Characterization of Bisphosphonic Carboxyfluorescein for Osteotropic Drug Delivery", J. Pharm. Pharmavol. 1996, 48, pp. 798-800.
Jakob et al., "Bone resorption parameters [carboxy-terminal telopeptide of type-I collagen (ICTP), amino-terminal collagen type-I telopeptide (NTx), and deoxypyridinoline (Dpd)] in MGUS and multiple myeloma", Eur. J. Haematol, 2002, 69, pp. 37-42.
Kowada et al., "In Vivo Fluorescence Imaging of Bone-Resorbing Osteoclasts", J. Am. Chem. Soc., 2011, 133, pp. 17772-17776.
Kozloff et al., "Validation of Fluorescent Pamidronate as Biomarker for Bisphosphonate Deposition and Retention in Vivo", 55th Annual Meeting of the Orthopaedic Research Society, 2009, Poster No. 621.
Lam et al., "Enumeration of Bone Microparticles in Plasma of Multiple Myeloma Patients", Clinical Lymphoma Myeloma and Leukemia, 2013, 13, p. S85, poster P-86.
Lee and Suzuki, "CTX Biochemical Marker of Bone Metabolism", Implant Dentistry, 2009, 18, pp. 492-500.
OsteoImage Mineralization Assay, Product Monograph, 2011.

(Continued)

*Primary Examiner* — Shafiqul Haq
(74) *Attorney, Agent, or Firm* — Santosh K. Chari; Blake, Cassels & Graydon LLP

(57) ABSTRACT

Methods for identifying subjects having bone loss by detecting bone microparticles in a sample of their bodily fluid are disclosed. Methods for monitoring bone loss and assessing efficacy of bone loss therapies by detecting bone microparticles in bodily fluid samples are also disclosed. Compounds for use as a negative control in the disclosed methods are provided as well as kits comprising such compounds.

8 Claims, 11 Drawing Sheets

(56) References Cited

OTHER PUBLICATIONS

Pecherstorfer et al., "Bone Resorption in Multiple Myeloma and in Monoclonal Gammopathy of Undetermined Significance: Quantification by Urinary Pyridinium Cross-Links of Collagen", Blood, 1997, 90, pp. 3743-3750.
Roodman, "Pathogenesis of myeloma bone disease", Leukemia, 2009, 23, pp. 435-441.
Terpos et al., "The use of biochemical markers of bone remodeling in multiple myeloma: a report of the International Myeloma Working Group", Leukemia, 2010, 24, pp. 1700-1712.
Zaheer et al., "Near-Infrared Fluorescence Imaging of Osteoblastic Activity", Proceedings of the American Association for Cancer Research, 2001, 42, p. 483, Abstract #2602.
International Search Report and Written Opinion issued on PCT/CA2014/050312 dated Jul. 17, 2014.

* cited by examiner

METHOD FOR DETECTING AND MONITORING BONE LOSS

CROSS REFERENCE TO PRIOR APPLICATIONS

This application claims priority under the Paris Convention from U.S. Application No. 61/805,471, filed on Mar. 26, 2013, which is incorporated herein by reference as if set forth in its entirety.

FIELD OF THE INVENTION

This invention relates generally to biochemical assays in the field of medicine. In particular, this invention is directed to methods and related materials for detecting and monitoring the progression of bone loss, in particular bone loss related to cancer, in mammalian subjects.

BACKGROUND OF THE INVENTION

Bone loss is a global health concern. The number of people, particularly women, afflicted with bone loss is increasing rapidly as the population over the age of 50 grows. Thus, strategies for detecting bone loss in its early stages are urgently needed.

Healthy bone is in a constant dynamic state of remodeling that is balanced by bone formation and breakdown (Coleman, Cancer Treat. Rev. 27:165-76, 2001). Bone loss occurs when there is a disruption to normal remodeling activity in the form of an increase in the breakdown of bone by osteoclasts without a comparable increase in bone building by osteoblasts. Bone loss can occur as part of the normal aging process (e.g., osteoporosis) or as a complication of cancer, such as bone cancer or bone metastases. Bone metastases can occur by way of the bloodstream when a cancer cell breaks away from a primary tumor and travels in the circulatory system until it becomes lodged in a small capillary network in bone tissue. Cancer cells release various factors that stimulate osteoclastic activity, disrupting bone remodeling balance and causing increased breakdown of bone, such as that which occurs in blood cancers, such as multiple myeloma (MM). Cancers that tend to metastasize to bone include breast, prostate, lung, kidney and thyroid cancers. Unfortunately, many therapies directed to cancer also promote bone loss. For example, hormonal therapies administered in the treatment of breast and prostate cancer can leave subjects more susceptible to bone loss and treatment with chemotherapy leads to bone loss in some subjects.

Osteolytic bone disease is a feature of MM that occurs in approximately 90% of patients during the course of their illness (Pecherstorfer et al., Blood, 90:3743-3750, 1997 and Terpos et al., Leukemia, 24:1700-1712, 2010). Skeletal related events (SREs) defined as 1) pathologic fracture, 2) spinal cord compression, 3) need for palliative radiotherapy, 4) need for orthopedic surgery, and 5) hypercalcemia are a significant source of pain and disability. Myeloma results in an uncoupling of the bone remodeling process, which leads to suppression of osteoblastic activity and upregulation of osteoclastic activity. The pathophysiology of myeloma bone disease involves, among other things, overproduction of the receptor activator of nuclear factor kB ligand (RANKL) by the malignant plasma cell clone. RANKL activates neighboring osteoclasts resident in the bone marrow leading to continuous bone degradation (Roodman, Leukemia 23:435-441, 2009).

Current standard clinical practice for diagnosing bone disease involves the skeletal survey, which comprises a series of plain film x-rays. However, this technique is relatively insensitive in that it requires a large amount of bone damage for positive detection. Further, skeletal survey is of limited use for monitoring a subject's response to treatment. For example, even after a patient has received anti-myeloma and bone-directed therapy, lytic lesions may persist. Other imaging modalities have been studied including CT, MRI, and PET but these techniques are cumbersome, expensive, and the subject of ongoing trials to determine their prognostic utility (Dimopoulos et al., Leukemia 23:1545-1556, 2009).

Bodily fluid-based diagnostic tests are advantageous relative to bone imaging techniques for several reasons including, for example, low invasiveness in sample collection (standard blood draw), low cost, and amenability to high throughput analyses. Such tests are particularly advantageous for monitoring subjects at risk for developing a disease, in part because they allow for collection of baseline data and continued data collection over time.

Dysregulated bone metabolism can be detected in a patient's blood or urine by measuring biochemical resorptive markers such as, for example, N-terminal cross-linked telopeptide (NTx), C-terminal cross-linked telopeptide (CTx), and the ratio of soluble RANKL to osteoprotegrin (sRANKL/OPG).

Currently, the CTx assay is not a standard test used to assess bone loss in MM patients due to high costs. Some studies advocate the use of CTx for MM disease prognosis (Jakob et al., Eur. J. Haematol. 69:37-42, 2002 and Abildgaard et al., Brit. J. Haematol. 120:235-242, 2003). However, larger studies of osteoporosis patients have raised questions regarding the assay's reliability due to a wide range of reference values (age and gender related) when setting up the assay and wide variability of results over a 24 hour period (Baim and Miller, J. Bone Mineral Res. 24:561-574, 2009; Avolio et al., Brazilian Oral Res. 24:250-255, 2010; Fleisher et al., Oral Surg. Oral Pathol. Oral Radiol. Endodontics 110:509-516, 2010; and Lee and Suzuki, Implant Dentistry 18:492-500, 2009).

The principal component of bone is hydroxyapatite, $Ca_5(PO_4)_3(OH)$ and hypercalcemia is a common feature of bone loss and MM. However, a caveat of bone loss assays that quantitate calcium in serum or plasma is that bone loss is likely not the principle source of calcium in the blood. Further, calcium lost from bone would not predominantly be in a 'soluble' ion form, which is measured in serum and plasma calcium assays.

SUMMARY OF THE INVENTION

The present invention is broadly summarized as relating to methods of detecting bone loss.

In an aspect, a method for detecting bone loss in a subject is provided. The method comprises measuring the amount of bone microparticles in a bodily fluid sample obtained from the subject. Bone microparticles are fragments of bone originating from bone tissue. Measuring the amount of bone microparticles comprises first exposing the bodily fluid sample to at least one labeled binding probe that is specific to hydroxyapatite, hydroxyapatite being a biomarker of bone microparticles and second measuring the amount of bone microparticles bound to the at least one labeled binding probe. The measured amount of bone microparticles bound to the at least one labeled binding probe is then compared with a reference value and detection of bone loss in the subject is based on results of the comparison.

In some embodiments, the reference value is derived from one or more samples obtained from one or more healthy subjects. In some embodiments, the reference value is derived from one or more samples obtained from one or more subjects having unhealthy bone loss. In some embodiments, bone loss is detected when the amount of measured bone microparticles is greater than the reference value derived from one or more samples obtained from one or more healthy subjects or greater than or equal to the reference value derived from one or more samples obtained from one or more subjects having unhealthy bone loss.

In some embodiments, the measurement of bone microparticles bound to the at least one labeled binding probe is obtained by flow cytometry. In some embodiments, flow cytometry is nanoscale flow cytometry.

In some embodiments, the bodily fluid is blood.

In some embodiments, the method further comprises effectuating a treatment based on the detection of bone loss.

In some embodiments, the subject has or is suspected of having cancer or osteoporosis.

In some embodiments, the at least one labeled binding probe comprises detectably-labeled Alendronate. In some embodiments, the measurement of bone microparticles bound to the at least one labeled binding probe is determined with reference to at least one isotype negative control of the at least one binding probe. In some embodiments, the at least one isotype negative control is fluorescently-labeled NOT-dronate. In some embodiments, the detectable label comprises a fluorophore. In some embodiments, the fluorophore is FITC or Cy5. In some embodiments, the at least one labeled binding probe comprises Alendronate-FITC and Alendronate-Cy5 and the at least one isotype negative control comprises NOT-dronate-FITC and NOT-dronate-Cy5.

In some embodiments, the reference value is in a range of 4500 to 6500 microparticle counts/µL.

In some embodiments, the bone microparticles have a diameter in a range of about 100 nm to 1 µm.

In an aspect, a method for monitoring bone loss in a subject is provided. The method comprises measuring the amount of bone microparticles in a first bodily fluid sample obtained from the subject at a first time point, bone microparticles being fragments of bone originating from bone tissue. Measuring comprises exposing the first bodily fluid sample to at least one labeled binding probe that is specific to hydroxyapatite, hydroxyapatite being a biomarker of bone microparticles; and then measuring the amount of bone microparticles bound to the at least one labeled binding probe. The amount of bone microparticles in a second bodily fluid sample obtained from the subject at a subsequent time point is also measured. Measuring comprising exposing the second bodily fluid sample to at least one labeled binding probe that is specific to hydroxyapatite; and then measuring the amount of bone microparticles bound to the at least one labeled binding probe in the second bodily fluid sample. The measured bone microparticles bound to the at least one labeled binding probe in the second bodily fluid sample are compared with the measurement obtained from the first bodily fluid sample. Increased or reduced bone loss in the subject is detected when there is a difference in the measurement obtained in step (a) (ii) relative to the measurement obtained in step (b) (ii).

In some embodiments, increased bone loss is detected when the measurement obtained from the first sample is less than the measurement obtained from the second sample or decreased bone loss is detected when the measurement obtained in the first sample is greater than the measurement obtained in the second sample.

In some embodiments, the measurement of bone microparticles bound to the at least one labeled binding probe is obtained by flow cytometry. In some embodiments, flow cytometry is nanoscale flow cytometry.

In some embodiments, the bodily fluid is blood.

In some embodiments, the method further comprises effectuating a treatment based on the detection of bone loss.

In some embodiments, the subject has or is suspected of having cancer or osteoporosis.

In some embodiments, the at least one labeled binding probe comprises detectably-labeled Alendronate. In some embodiments, the measurement of bone microparticles bound to the at least one labeled binding probe is determined with reference to at least one isotype negative control of the at least one binding probe. In some embodiments, the at least one isotype negative control is fluorescently-labeled NOT-dronate. In some embodiments, the detectable label comprises a fluorophore. In some embodiments, the fluorophore is FITC or Cy5. In some embodiments, the at least one labeled binding probe comprises Alendronate-FITC and Alendronate-Cy5 and the at least one isotype negative control comprises NOT-dronate-FITC and NOT-dronate-Cy5.

In some embodiments, the reference value is in a range of 4500 to 6500 microparticle counts/µL.

In some embodiments, the bone microparticles have a diameter in a range of about 100 nm to 1 µm.

In an aspect, a method for assessing efficacy of a therapy on a subject having bone loss is provided. The method comprises measuring the amount of bone microparticles in a first bodily fluid sample obtained from the subject at a first time point, the subjected having been subjected to a bone loss-directed therapy, bone microparticles being fragments of bone originating from bone tissue. The measurement comprises exposing the bodily fluid sample to at least one labeled binding probe that is specific to hydroxyapatite, hydroxyapatite being a biomarker of bone microparticles and measuring the amount of bone microparticles bound to the at least one labeled binding probe. The measurement obtained from the first sample is compared with a reference value. Efficacy of the therapy is determined based on results of the comparison.

In some embodiments, the reference value is derived from a bodily fluid sample obtained from the subject at a time point prior to the first time point. Poor efficacy is detected when the measurement obtained from the first sample is greater than the reference value or good efficacy is detected when the measurement obtained from the first sample is less than the reference value.

In some embodiments, the measurement of bone microparticles bound to the at least one labeled binding probe is obtained by flow cytometry. In some embodiments, flow cytometry is nanoscale flow cytometry.

In some embodiments, the bodily fluid is blood.

In some embodiments, the method further comprises effectuating a treatment based on the detection of bone loss.

In some embodiments, the subject has or is suspected of having cancer or osteoporosis.

In some embodiments, the at least one labeled binding probe comprises detectably-labeled Alendronate. In some embodiments, the measurement of bone microparticles bound to the at least one labeled binding probe is determined with reference to at least one isotype negative control of the at least one binding probe. In some embodiments, the at least one isotype negative control is fluorescently-labeled NOT-dronate. In some embodiments, the detectable label comprises a fluorophore. In some embodiments, the fluorophore is FITC or Cy5. In some embodiments, the at least one labeled binding probe comprises Alendronate-FITC and Alendronate-Cy5 and the at least one isotype negative control comprises NOT-dronate-FITC and NOT-dronate-Cy5.

In some embodiments, the reference value is in a range of 4500 to 6500 microparticle counts/μL.

In some embodiments, the bone microparticles have a diameter in a range of about 100 nm to 1 μm.

In an aspect, a kit for detecting bone loss in a bodily fluid sample is provided. The kit comprises a first labeled isotype negative control for labeled Alendronate, Alendronate being specific to hydroxyapatite and hydroxyapatite being a biomarker of bone microparticles.

In some embodiments, the kit further comprises a first labeled binding probe, the labeled binding probe being Alendronate.

In some embodiments, the first labeled binding probe is Alendronate-Cy5 and the first isotype negative control is NOT-dronate-Cy5.

In some embodiments, the kit further comprises a second labeled binding probe specific to hydroxyapatite, and a second isotype negative control for the second labeled binding probe specific to hydroxyapatite. In some embodiments, the second labeled binding probe is Alendronate-FITC and the second isotype negative control is NOT-dronate-FITC.

In some embodiments, the kit further comprises one or more media, reagents, vessels or instructions for using the kit.

In an aspect, a compound represented by formula (I):

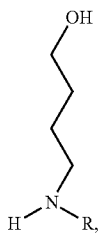

wherein R is a detectable label, is provided.

In some embodiments, the detectable label is a fluorophore. In some embodiments, the fluorophore is FITC or Cy5.

In an aspect, use of a compound represented by formula (I):

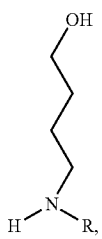

wherein R is a detectable label, as a labeled isotype negative control for labeled Alendronate in a protein assay is provided. In some embodiments, the protein assay is a flow cytometry assay, a pull-down assay, immunohistochemistry staining or a mass spectrometry assay. In some embodiments, the compound is used in a method for detecting bone microparticles in bodily fluid sample. In some embodiments, the compound is used in a method for detecting bone loss, monitoring bone loss or assessing efficacy of a bone loss therapy, provided herein.

BRIEF DESCRIPTION OF THE DRAWINGS

The features of the invention will become more apparent in the following detailed description in which reference is made to the appended drawings wherein.

compared to its isotype negative control (C). Dual positive events exhibit a size distribution of 304 nm-585 nm when events in the red gate of A) are transposed in a sizing histoplot (B). Background in this sample is minimized (fewer events in red gate of panel C) when both AL-FITC and AL-Cy5 is used to detect dual-positive bone microparticles in plasma. This MGUS patient plasma had high counts of bone microparticles, as determined by dual-staining with Alendronate-FITC and Alendronate-Cy5.

Figure 6:
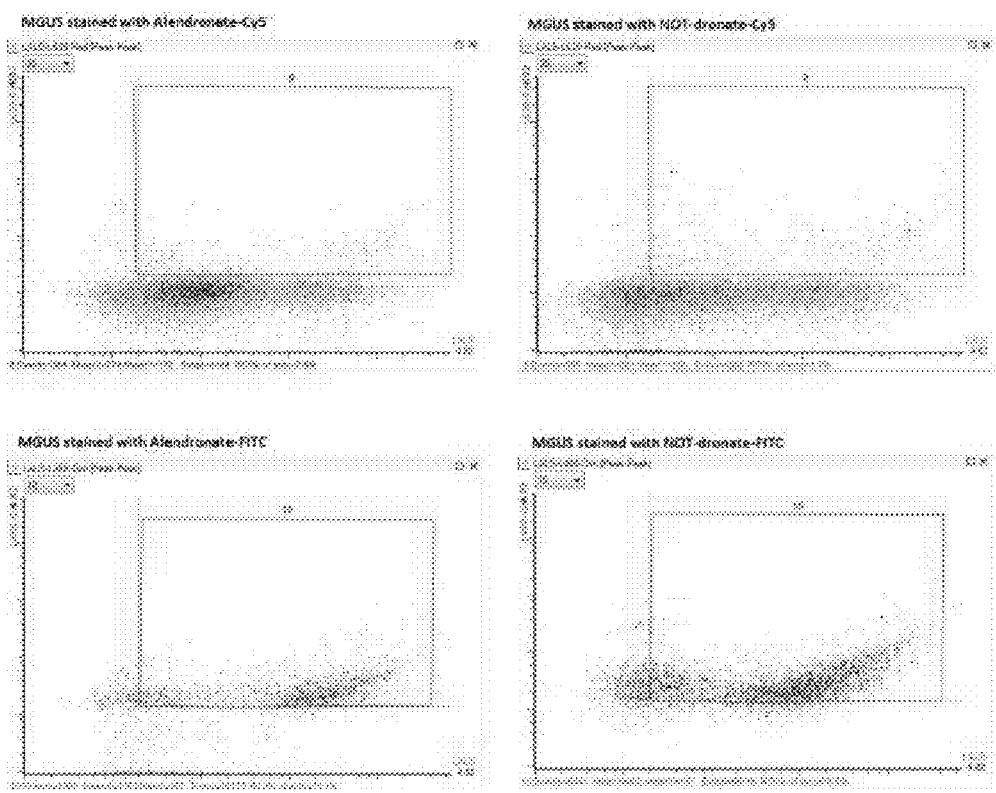

FIG. 6 depicts detection of bone microparticles in plasma from another patient with MGUS single stained with Alendronate-FITC (AL-FITC) or Alendronate-Cy5 (AL-Cy5). Plasma from this patient with MGUS was incubated with AL-Cy5 (A) or AL-FITC (C) and its negative isotype controls, NT-Cy5 (B) and NT-FITC (D). No difference was observed between AL-Cy5 stained plasma (A) and NT-Cy5 stained plasma (B). When using AL-FITC and NT-FITC, a higher count of events was observed in the NT-FITC negative control stained sample (D) compared to the AL-FITC stained sample (C).

Figure 7:
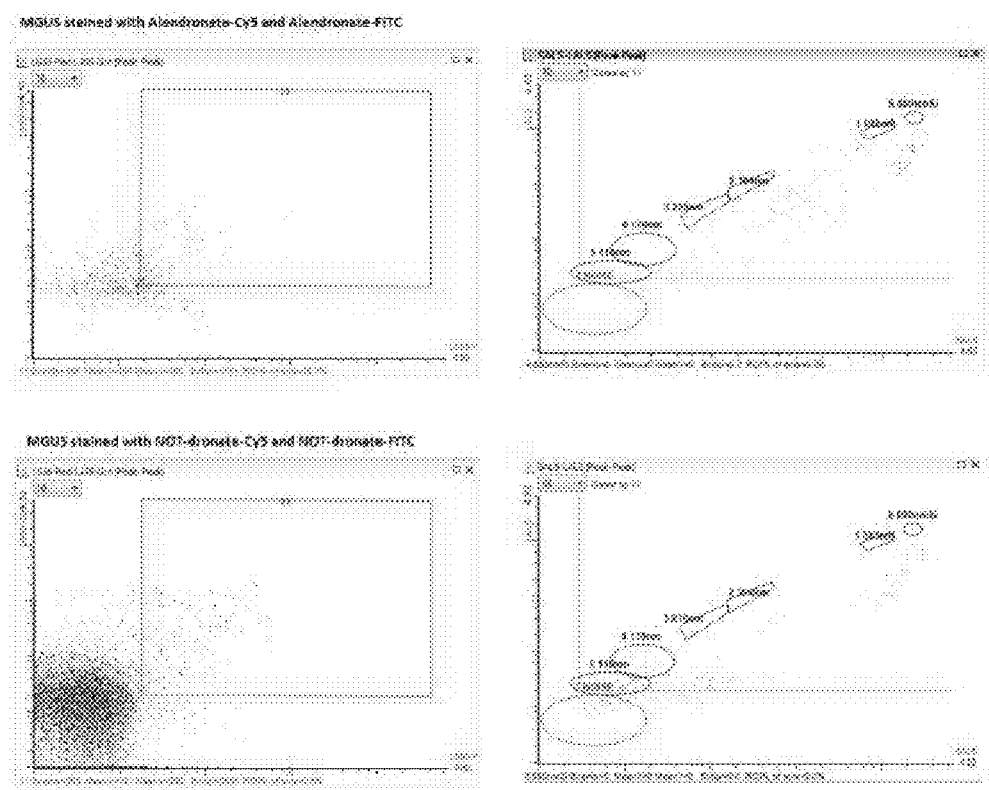

FIG. 7 depicts detection of dual positive AL-FITC and AL-Cy5 bone microparticles in plasma from the patient with MGUS of FIG. 6. Plasma was incubated with AL-FITC and AL-Cy5 (A, B) or its negative isotype controls, NT-FITC and NT-Cy5 (C, D). Few dual-positive events were found in the AL-FITC and AL-Cy5 dual stained sample (A) compared to its isotype negative control (C). Dual positive events exhibit a size distribution of 304 nm-585 nm when events in the red gate of (A) are transposed in a sizing histoplot (B). Background in this sample is again minimized (fewer events in red gate of panel C) when both AL-FITC and AL-Cy5 is used to detect dual-positive bone microparticles in plasma. Few bone microparticles were detected by this method in this MGUS patient plasma sample.

Figure 8:
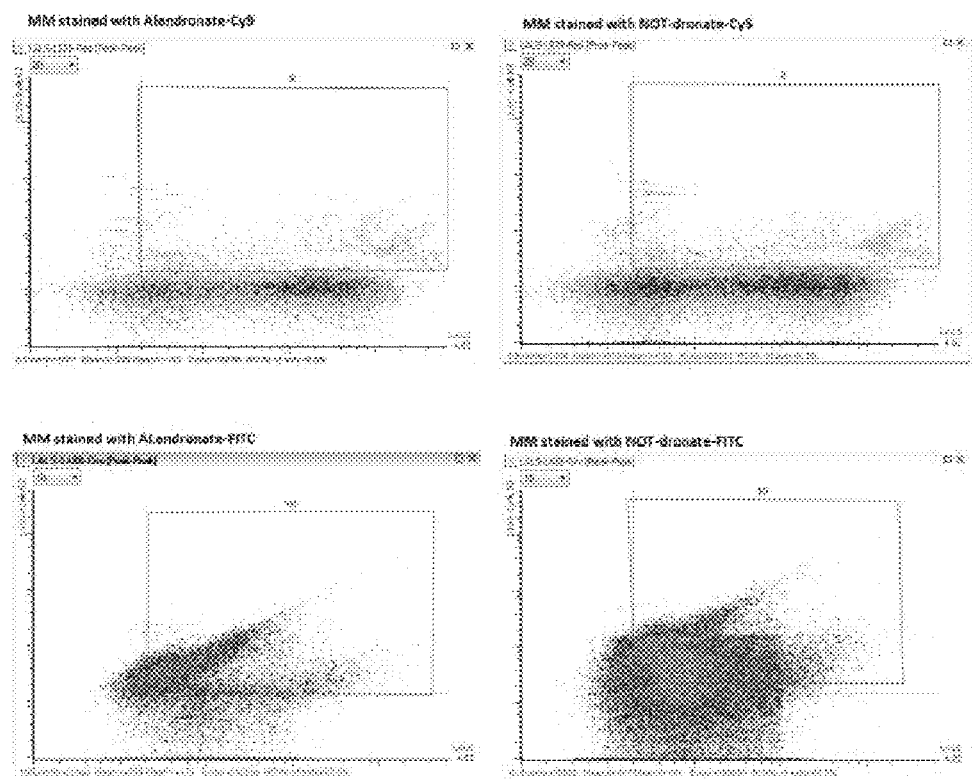

FIG. 8 depicts detection of bone microparticles in plasma from a patient with Multiple Myeloma (MM) single stained with Alendronate-FITC (AL-FITC) or Alendronate-Cy5 (AL-Cy5). Plasma from a patient with Multiple Myeloma (MM) was incubated with AL-Cy5 (A) or AL-FITC (C) and its negative isotype controls, NT-Cy5 (B) and NT-FITC (D). No difference was observed between AL-Cy5 stained plasma (A) and NT-Cy5 stained plasma (B). When using AL-FITC and NT-FITC, a higher count of events was observed in the NT-FITC negative control stained sample (D) compared to the AL-FITC stained sample (C).

Figure 9:
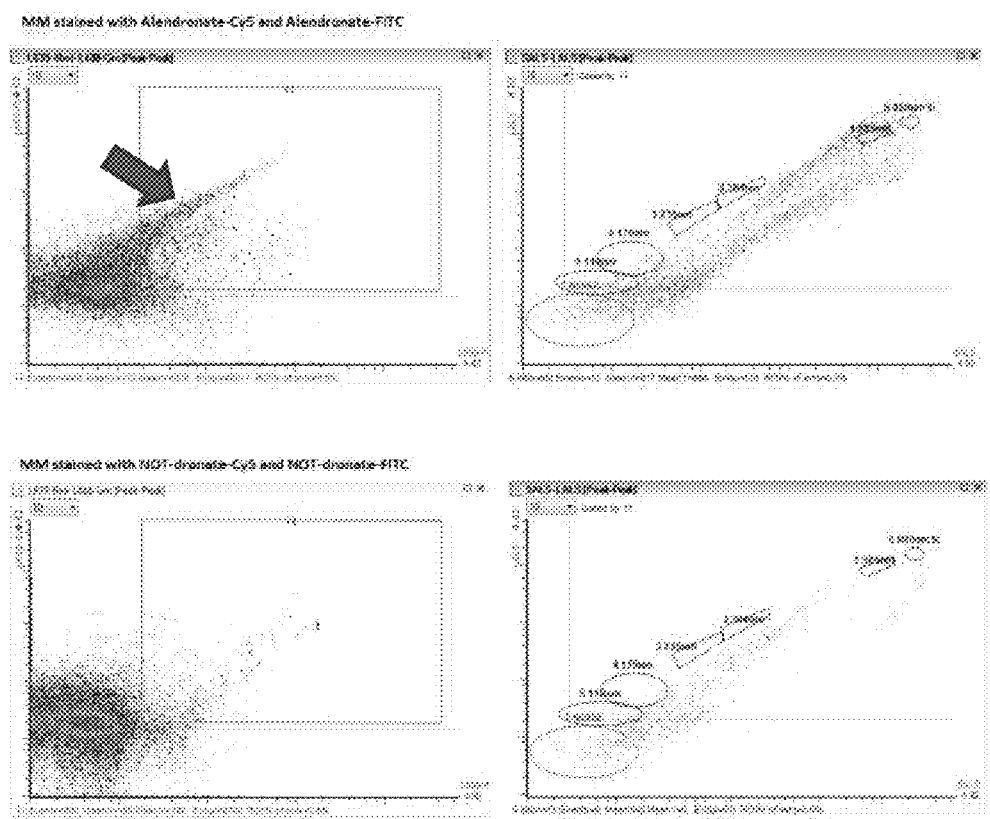

FIG. 9 depicts detection of dual positive AL-FITC and AL-Cy5 bone microparticles in plasma from a patient with Multiple Myeloma (MM). Plasma was incubated with AL-FITC and AL-Cy5 (A, B) or its negative isotype controls, NT-FITC and NT-Cy5 (C, D). A significant population of dual-positive events were found in the AL-FITC and AL-Cy5 dual stained sample (A, arrowhead) compared to its isotype negative control (C). Dual positive events exhibit a size distribution of 110 nm-585 nm when events in the red gate of (A) are transposed in a sizing histoplot (B). Background in this sample is minimized (fewer events in red gate of panel C) when both AL-FITC and AL-Cy5 is used to detect dual-positive bone microparticles in plasma.

Figure 10:
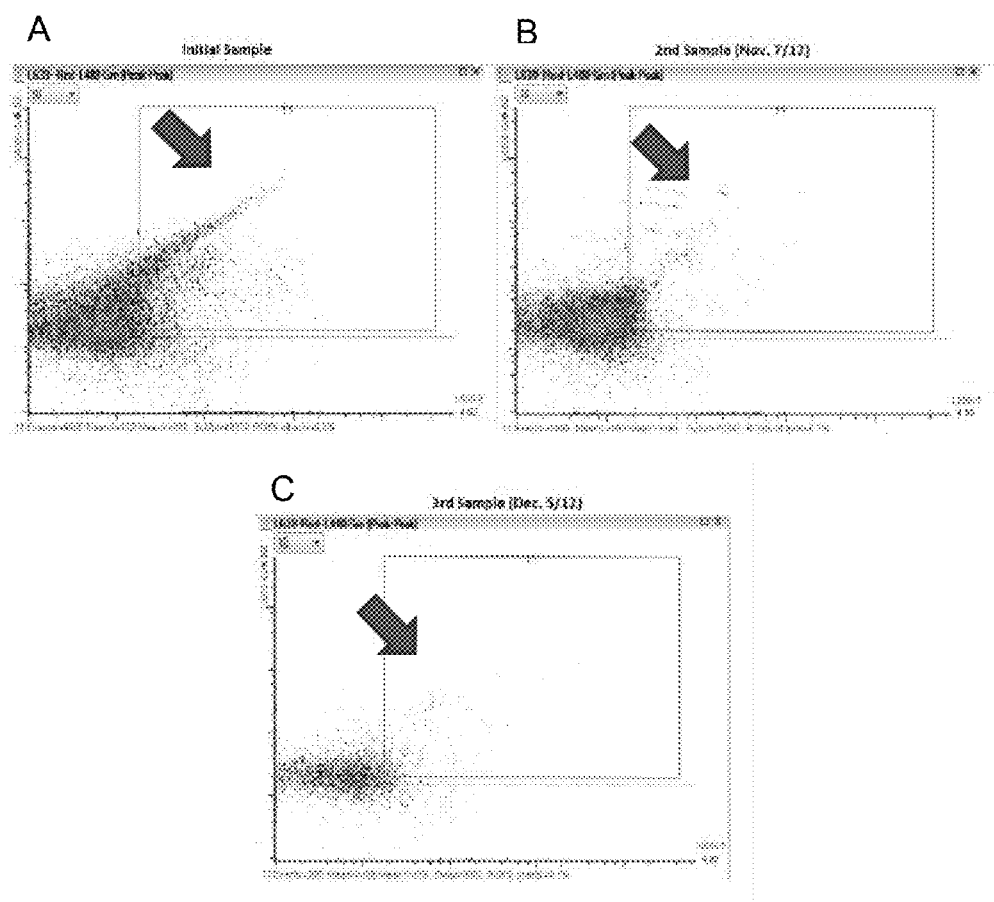

FIG. 10 depicts a longitudinal analysis of dual positive AL-FITC and AL-Cy5 bone microparticles in plasma from a patient with Multiple Myeloma (MM) treated with chemotherapy. When staining for dual-positive bone microparticles (AL-FITC and AL-Cy5), a significant population was observed at the initial sample prior to administration of chemotherapy (A). The plasma sample collected two weeks later after chemotherapy revealed a loss of the bone microparticle population (B, black arrowhead). The third plasma sample (C) reveals a loss of that same population indicating that no bone microparticles are present in the blood.

Figure 11:
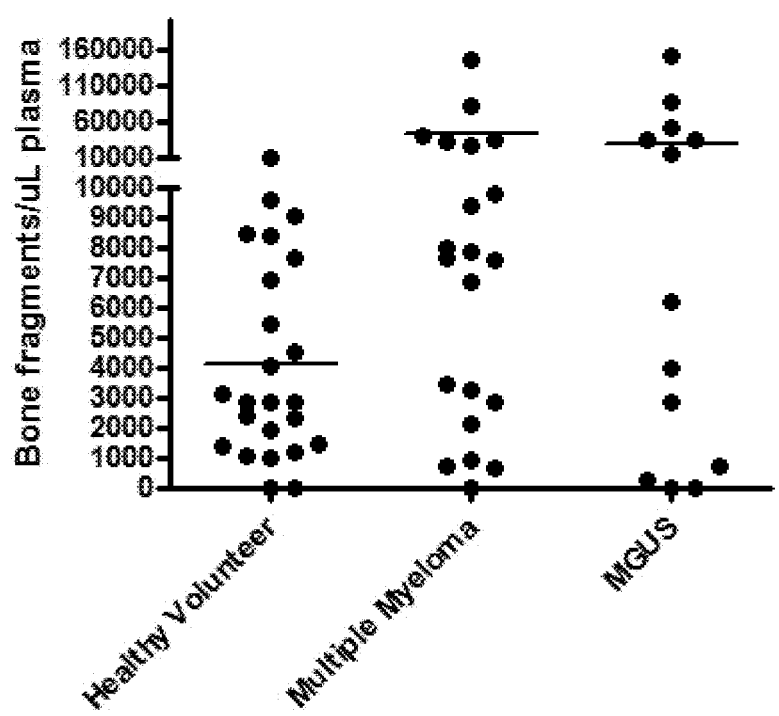

FIG. 11 depicts bone microparticle counts in the plasma of Healthy Volunteer, Multiple Myeloma and MGUS patient cohorts. Healthy volunteer plasmas exhibit a wide range of bone microparticle counts but the mean is lower compared to the Multiple Myeloma cohort and the MGUS cohort. The majority of Multiple Myeloma patients have higher AL-Cy5+AL-FITC counts compared to Healthy Volunteers. The MGUS cohort has a subpopulation of patients that exhibit high bone microparticle counts according to the method disclosed herein.

DETAILED DESCRIPTION OF THE INVENTION

The definitions of certain terms as used in this specification are provided below. Unless defined otherwise, all technical and scientific terms used herein generally have the same meaning as commonly understood by one of ordinary skill in the art to which this invention belongs.

As used herein, the term "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the enumerated value.

As used herein, the terms "diagnose", "diagnosing" and "diagnostic" refer to the process of determining a disease state or disorder in a subject. In determining disease state a diagnostician might classify one or more characteristics of a subject, such as, for example, symptoms and/or biomarkers. A "diagnostic assay" is referred to herein as a tool that a diagnostician might use to narrow the diagnostic possibilities.

As used herein, the term "subject" refers to a mammal, such as, for example, a human, non-human primate, mouse, rat, dog, cat, horse, or cow. In some embodiments, a subject is human and might be referred to as a patient. A subject can be one who has been previously diagnosed or identified as having a disease, and optionally one who has already undergone, or is undergoing, a therapeutic intervention for a disease. Alternatively, a subject can also be one who has not been previously diagnosed as having a disease.

As used herein, the terms "bodily fluid sample" and "fluid sample" refer to a specimen obtained from a subject. In some embodiments, the sample comprises blood, a fraction of blood or urine.

As used herein, the terms "detect", "detection" and "detecting" refer to a quantitative or qualitative determination of a property of an entity, for example, quantifying the amount or concentration of a molecule or the activity level of a molecule. The term "concentration", "amount" or "level" can refer to an absolute or relative quantity. Measuring a molecule may also include determining the absence or presence of the molecule. Various methods of detection are known in the art, for example fluorescence analysis. In this regard, biomarkers can be measured using fluorescence detection methods, or other methods known to the skilled artisan.

As used herein, the term "bone microparticle" refers to small fragments of bone (generally about 100 nm to 1 μm in diameter) originating from bone tissue. Bone microparticles circulate in blood and are derived from bones in contact with the bloodstream. Bone microparticles are useful in various embodiments of the present invention, at least because they retain at least some of the molecular characteristics of their parent tissue.

As used herein, the term "biomarker" refers to a molecule whose measurement provides information regarding the state of a subject, such as, for example, the disease state of a subject. Measurements of the biomarker may be used alone or combined with other data obtained regarding a subject in order to determine the state of the subject. In one embodiment, the biomarker is "differentially present" in a sample taken from a subject of one disease state (e.g., having a disease) as compared with another disease state (e.g., not having the disease). In one embodiment, the biomarker is "differentially present" in a sample taken from a subject undergoing no therapy or one type of therapy as compared with another type of therapy. Alternatively, the biomarker may be "differentially present" even if there is no known difference in disease state, e.g. the biomarkers may allow the detection of asymptomatic risk.

As used herein, the terms "specific" and "specificity" refer to the nature of the binding of a biomarker with its binding probe. "Specific binding" or "selective binding" refers to a probe that binds the biomarker with a specificity sufficient to differentiate between the biomarker and other components or contaminants of the test sample.

As used herein, the term "reference value" refers to a baseline value. A baseline value represents the number of bone microparticles in a composite sample from an effective number of subjects who do not have the disease of interest and who are positive for the biomarker of interest. A reference value can also comprise the number of bone microparticles in a composite sample from an effective number of subjects who have the disease of interest, as confirmed by an invasive or non-invasive technique.

As used herein, the terms "indicative of", "associated with" and "correlated to" refer to the determination of a relationship between one type of data with another or with a state. In some embodiments, correlating the measurement with disease comprises comparing the number of bone microparticles positive for a biomarker with a reference value. In some embodiments, correlating the measurement with disease comprises determining the subject's disease state.

As used herein, the terms "treatment", "treatment regimen", "therapy" and "therapeutic treatment" refer to an attempted remediation of a health problem. In some embodiments, treatment can be selected from, administering a disease-modulating drug to a subject, administering disease-modulating radiation to a subject, surgery or scheduling for a further appointment with a medical practitioner. Treatment refers to initiating therapy, continuing therapy, modifying therapy or ending therapy.

As used herein, the term "bone loss-directed therapy" refers to an attempt to remediate undesirable bone loss in a subject.

As used herein, the terms "prophylaxis" and "prophylactic" refer to measures taken to prevent disease. Prophylactic treatment includes, for example, measures to reverse, prevent or slow down physiological features that are precursors to disease.

As used herein, the term "binding probe" refers to compounds that are used to detect the presence of, or to quantify, relatively or absolutely, a target molecule or target sequence and that will bind to the target molecule or sequence, either directly or indirectly. Generally, the binding probe allows attachment of a target molecule or sequence to the probe for the purpose of detection. In some embodiments, the target molecule or sequence is a biomarker. It follows that the composition of the binding probe will depend on the composition of the biomarker. Binding probes for a variety of biomarkers are known or can be generated using known techniques. For example, when the biomarker is a protein, the binding probes include for example, small molecules and proteins.

As used herein, the terms "label" and "labeled" refer to a composition detectable by spectroscopic, photochemical, biochemical, immunochemical, chemical, or other physical means. A compound that is labeled has at least one molecule, element, isotope or chemical compound attached to it to enable the detection of the compound. For example, useful labels include fluorescent dyes, which might also be referred to as fluorophores.

As used herein, the term "fluorophore" refers to a molecule or part of a molecule that absorbs energy at one wavelength and re-emits energy at another wavelength. Detectable properties of fluorophores include fluorescence intensity, fluorescence lifetime, emission spectrum characteristics, energy transfer, and the like. Fluorophores are of use in various embodiments of the present invention, at least due to their strong signals, which provide a signal-to-noise ratio sufficient to allow interpretation of the signals. Suitable fluorophores include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue, Texas Red, Alexa dyes and others described in the 6th Edition of the Molecular Probes Handbook by Richard P. Haugland.

As used herein the term "negative control" refers to an element or group used in an experiment to ensure that a negative result is produced when a negative result is expected. For example, a negative control binding probe, as referred to herein, is a probe that should not bind to the bone microparticle being examined because the probe's component that is responsible for specific binding is not present in the sample being examined. Thus, when assayed, if a negative control binding probe successfully binds to a sample, then it can be inferred that a confounding variable acted on the experiment, suggesting that the positive results are likely not due the intended specific binding.

As used herein, the term "monitoring" refers to the observation of a disease over time. Monitoring of a subject's disease state can be performed by continuously measuring certain parameters and/or by repeatedly performing a medical test. In some embodiments of the present invention, a subject's disease state is monitored by repeatedly obtaining bodily fluid samples, assaying the samples using the method disclosed herein and comparing the results of the assays with one another and/or with a reference value to identify any change in the subject's disease state.

As used herein, the term "disease state" refers to any distinguishable manifestation of a particular disease, including non-disease. For example, disease state includes, without limitation, the presence or absence of a disease, the risk of developing the disease, the stage of the disease, the progression or remission of the disease over time and the severity of disease. The term "worsened disease state" refers to the progression of disease over time. The term "improved disease state" refers to lessening of disease over time.

As used herein, the term "healthy bone state" or "healthy" refers to a subject having bones with balanced bone remodeling.

As used herein, the term "bone loss" or "unhealthy bone loss" refers to a subject having bones with unbalanced bone remodeling, wherein imbalance is the result of either and increase in the breakdown of bone by osteoclasts without a comparable increase in bone building by osteoblasts or a decrease in bone building by osteoclasts without a comparable decrease in bone breakdown by osteoclasts.

As used herein, the term "efficacy" refers to the capacity of an intervention to produce a therapeutic effect. For example, a bone loss treatment having good efficacy might significantly reduce the amount of bone loss from a subject or significantly increase the amount of bone generation in a subject. In contrast, a bone loss treatment having a poor efficacy might not reduce bone loss in a subject.

As used herein, the term "kit" refers to a collection of elements that together are suitable for a defined use.

As used herein, the term "invasive" refers to a medical procedure in which a part of the body is entered, wherein entry into the body might cause a subject to feel pain during or following the procedure. For example, surgical procedures involving incisions are invasive. For the purposes of the present description, a standard blood draw is not considered to be invasive.

The present invention is based on the inventors' hypothesis that a subjects may have bone microparticles in their blood. The inventors further hypothesized that quantification of bone microparticles in a subject's blood might provide a means of detecting bone loss. Previously, it was not known whether bone microparticles were present in blood and it was not known whether bone fragments could be released from sites of osteolysis (bone breakdown) and enter the blood. Based on the chemical composition of hydroxyapatite ("HA", written as $Ca_5(PO_4)_3(OH)$), a primary component of bone, the inventors synthesized fluorophore-conjugated bisphosphonates, which were design to bind specifically to the HA in bone. In some aspects, two fluorophore-conjugated bisphosphonates having distinct fluorophores can be used to detect bone microparticles in a bodily fluid sample.

Some embodiments involve a method for diagnosing bone loss in a subject having cancer. The method comprises obtaining a bodily fluid sample from the subject, for example a blood sample. In some embodiments of the method, the blood sample can be fractionated to obtain platelet poor plasma.

The fractionated sample is then analyzed, for example by a flow cytometry assay, to specifically detect bone microparticles using a fluorescently-labeled binding probe specific to HA. The presence of HA is sufficient to identify a microparticle as a bone microparticle. In some embodiments, flow cytometry is carried out using a nanoscale flow cytometer.

In some embodiments, the fluorescently-labeled binding probe specific to HA is Alendronate-FITC or Alendronate-Cy5. Alendronate is a bisphosphonate that specifically binds to HA in bone tissue. Detection of microparticles containing HA allows for specific identification of a sample containing bone microparticles.

In some embodiments, the number of bone microparticles identified in a sample by the flow cytometry assay is compared with a reference value.

The reference value can be a baseline number that represents the amount of bone microparticles that are found in a given volume of sample from a typical subject who has a healthy bone state. Where a reference value is indicative of a healthy bone state, a measured value in a subject that is greater than said reference value would be indicative of unhealthy bone loss in the subject. It is also contemplated herein that a reference value could, in contrast, represent the amount of bone microparticles that are found in a given volume of sample from a subject having unhealthy bone loss. Where such a reference value is used, a measured value in a subject that is less than said reference value would be indicative of a healthy bone state in the subject; a measured value in a subject that is greater than or equal to said reference value would be indicative of unhealthy bone loss in the subject. In some embodiments, the reference value is in a range of about 4500-6500 bone microparticle counts/µL and a value above about 6500 bone microparticle counts/µL is indicative of bone loss.

In some embodiments, the method can yield a result indicative of unhealthy bone loss. Treatments for bone loss are known in the art. A treatment for bone loss can be selected from, for example, administering a medication, such as, for example, a bisphosphonate, to a subject, administering calcium and/or vitamin D supplements to a subject, lifestyle changes, such as, for example, increasing physical activity and/or decreasing tobacco and alcohol consumption or scheduling for a further appointment with a medical practitioner.

In some embodiments, the method can yield a result indicating that bone loss is not present in the patient sample. In such instance, further monitoring of the patient may be recommended by way of further tests or visits to a medical practitioner over time.

In some embodiments, the flow cytometry assay comprises exposing a bodily fluid sample to a composition comprising at least one labeled binding probe that is specific to HA, for example, Alendronate. In some embodiments, the at least one binding probe is labeled with a fluorophore. In some embodiments, the composition comprises two differently labeled binding probes specific to HA. In some embodiments, the labels are fluorophores. When selecting suitable fluorophores the excitation wavelength of the fluorophore conjugated to the first of the two binding probes should be distinct from the excitation wavelength of the fluorophore conjugated to the second of the two binding probes.

Suitable fluorophores include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue, Texas Red, Alexa dyes and others described in the 6th Edition of the Molecular Probes Handbook by Richard P. Haugland. In some embodiments, Cyanine-5 (Cy5) is conjugated to the first binding probe and flourescein isothiocyanate (FITC) is conjugated to the second binding probe. Use of two fluorescent binding probes specific to HA is preferable, at least because it allows for detection of non-specific binding of fluourescently-labeled probes.

In some embodiments, negative controls are used in the method of detecting bone loss, to allow for quantification of microparticles that are positive for HA.

The inventors were not aware of any negative controls that would be suitable for use with Alendronate in a flow cytometry assay (including a nanoscale flow cytometry assay). Therefore, the inventors synthesized a suitable negative control, which is a fluorescently-labeled molecule referred to herein as "NOT-dronate", wherein NOT-dronate is represented by formula (I):

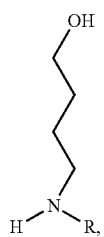

wherein R is a fluorophore. In some embodiments, the first negative control is NOT-dronate-Cy5 and the second negative control is NOT-dronate-FITC.

In some embodiments of the method, a portion of the sample of the bodily fluid is removed and exposed to a composition comprising the first and second negative control binding probes, such as NOT-dronate-Cy5 and NOT-dronate-FITC. The exposed sample is then analyzed by a flow cytometry assay to specifically detect microparticles bound to fluorescent labels in the bodily fluid sample. If any microparticles are found to bind to one or more of the negative control probes, then a confounding variable might be responsible for any fluorescent microparticles that are identified in the disclosed assay for detecting bone microparticles. If the fluorescence of the negative control probes is not observed, then confounding variables can be eliminated as possible cause for positive results that are found in the disclosed assay for detecting HA-positive bone microparticles.

In some embodiments, a diagnostic assay for bone loss is provided, wherein the assay comprises one or more embodiments of the methods set forth above, and disclosed further in the examples herein.

In some embodiments, a method for monitoring bone loss in a subject is provided. In some monitoring methods, a first fluid sample is obtained from the subject at a first time point. The first sample is then subjected to analysis comprising measurement of the amount of bone microparticles in the sample. The monitoring method can further comprise, obtaining a second bodily fluid sample from the subject at a second time point subsequent to the first time point. The second sample is then subjected to analysis comprising measurement of the amount of bone microparticles in the sample. The measurement obtained from the second sample is compared to the measurement obtained from the first sample to determine if the subject's disease state has improved, worsened or remained constant since the first time point. A treatment regimen can then be effectuated based on the subject's disease state. The treatment might involve, for example, drug, nutrient supplement or lifestyle intervention or it might involve further monitoring as discussed below.

Monitoring of bone loss can further involve collecting, analyzing and comparing the analytical results from a series of samples taken from the subject over a series of time periods.

The monitoring method can also provide an opportunity to assess the efficacy of any treatment that was provided to the subject during the time in which samples were obtained from the subject. A subsequent measurement indicating improved disease state would be indicative of a treatment being effective. A subsequent measurement indicating worsened disease state would be indicative of a treatment having poor efficacy.

In some embodiments, a method is provided for assessing efficacy of a therapy on a subject having bone loss, wherein repeated sampling of a patient is not required. In such methods, a bodily fluid sample is obtained from a subject treated with a bone loss therapy. The sample is then analyzed and compared to a reference sample as set forth above and described further in the examples below. The measured value obtained from the sample is then compared to the reference value to determine if bone loss has occurred. Such a method might be advantageous for determining whether a drug treatment has successfully re-balanced the bone remodeling process in a subject.

It is contemplated herein that the disclosed methods are useful for monitoring bone loss in a subject having cancer or suspected of having cancer. It is also contemplated that disclosed methods could be used to detect cancer, such as, for example, bone cancer, bone metastases and multiple myeloma (MM).

In some embodiments, the method is sensitive. Bone density scans require large amounts of bone degradation to have occurred in order to generate positive results. In contrast, it is contemplated herein that disclosed methods of detecting bone loss can be used to detect very early stages of bone loss in subjects undergoing osteolytic processes, such as those involved with cancer, wherein very small microparticles of bone are released from diseased bone into the blood stream.

In some embodiments, the methods are amenable to high throughput, and require small sample sizes, such as, for example, 20 µL. Such methods are therefore expected to be inexpensive relative to bone scans. A blood test to quantify bone loss, such as that recited in methods disclosed herein, would be useful for monitoring cancer patients at risk for bone metastasis. In some embodiments, the measurement step of the method allows the impact of a therapeutic intervention to be assessed by measuring the total change of bone microparticles in a subject's blood before and after therapy.

It is contemplated herein that some embodiments of the present invention can be used to detect and monitor bone loss in subjects having osteoporosis or who are at risk for developing osteoporosis.

In some embodiments, a kit is provided for detecting bone loss in a bodily fluid sample. The kit comprises a first labeled isotype negative control for labeled Alendronate, Alendronate being specific to hydroxyapatite, hydroxyapatite being a biomarker of bone microparticles. The kit may further comprise a first labeled binding probe specific to HA, such as Alendronate. In some embodiments, the first labeled binding probe is Alendronate-Cy5. In some embodiments, the first isotype negative control is NOT-dronate-Cy5.

In some embodiments, the kit further comprises a second labeled binding probe specific to HA, and a second isotype negative control for the second labeled binding probe specific to hydroxyapatite. In some embodiments, the second labeled binding probe is Alendronate-FITC. In some embodiments, the second isotype negative control is NOT-dronate-FITC.

In some embodiments, the kit provides the first and second binding probes in a first sealed container. In some embodiments, the negative controls are provided in a second sealed container.

In some embodiments, the kit might comprise a carrier, such as a box, carton, tube or the like, having disposed therein one or more sealed containers, such as vials, tubes, ampoules, bottles, pouches, envelopes and the like. In some embodiments, the kit might comprise one or more media or media ingredients or reagents for the measurement of the various biomarkers disclosed herein. For example, kits may also comprise, in the same or different containers, one or more suitable buffers or probes. The kits may also comprise one or more instructions or protocols for carrying out embodiments of the present invention.

In some embodiments of the present invention a compound having the structure of formula (I):

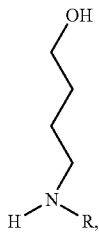

wherein R is a detectable label. The detectable label can make the NOT-dronate molecule useful as a probe. The compound of formula (I) is referred to as NOT-dronate. In some embodiments, NOT-dronate can be used as a negative control for labeled Alendronate in a protein assay. In some embodiments NOT-dronate molecules are labeled with fluorophores such as, for example, Cy5 or FITC.

It is contemplated herein that labeled NOT-dronate molecules could be useful as negative controls in other flow cytometry methods that use binding probes having detectable labels to identify agents such as, for example, molecules or proteins. It is also contemplated that labeled NOT-dronate could be used as a negative control in pull-down assays, immunohistochemistry staining and mass spectrometry assays.

EXAMPLES

The present invention is further illustrated by the following examples, which should not be construed as limiting in any way.
Materials and Methods
Subjects:
Three groups of subjects were sampled. The first, "healthy volunteers", were healthy individuals over the age of 18 with no known history of multiple myeloma or known evidence of active malignancy. The second, "patients with MGUS (monoclonal gammopathy of undetermined significance)", were over 18 years old and initially referred to the myeloma clinic with a monoclonal gammopathy. MGUS patients met the diagnostic criteria as defined by the IMWG (International Myeloma Working Group): monoclonal gammopathy with m-protein <30 g/L, bone marrow plasma cells <10%, and no evidence of end organ damage (no anemia, hypercalcemia, renal insufficiency, or lytic bone disease). The third, "multiple myeloma patients", were over 18 years old and initially referred to the myeloma clinic with a new diagnosis of multiple myeloma as defined by IMWG criteria (see below).

All Patients had i) blood samples drawn prior to any chemotherapy or bone directed therapy (i.e. bisphosphonates), ii) presence of monoclonal protein in blood or urine, iii) >10% bone marrow plasma cells, and iv) presence of myeloma-related end organ damage including one of anemia (hemoglobin <100 g/L), hypercalcemia (calcium >2.75 mmol/L), renal insufficiency (creatinine >173 mmol/L), or bone lesions (lytic bone disease, osteopenia, pathologic fracture).

Plasma Preparation:
7 ml blood was collected into Sodium-Heparin BD Vaccutainers (BD Biosciences; Cat#3678800). To separate plasma from the erythrocyte fraction of blood, blood was spun down at 1500 g's for 10 minutes at 24° C. in an Eppendorf Centrifuge 5810 R. Plasma was removed from the vaccutainer in 1 ml quantities and transferred into 1.7 mL microtubes tubes (Frogga Bio; Cat#1260-00). To remove any remaining platelets or erythrocytes microcentrifuge tubes were spun down at 7000 rpm for 5 minutes at room temperature in and Eppendorf Centrifuge 5415 C. Plasma was transferred into 1.5 ml cryovials (Sarstedt; Cat#72.694.006) in 0.5 ml aliquots and stored at −80° C.

Synthesis of Probes:
AS-01-077A (Alendronate-Cy5):

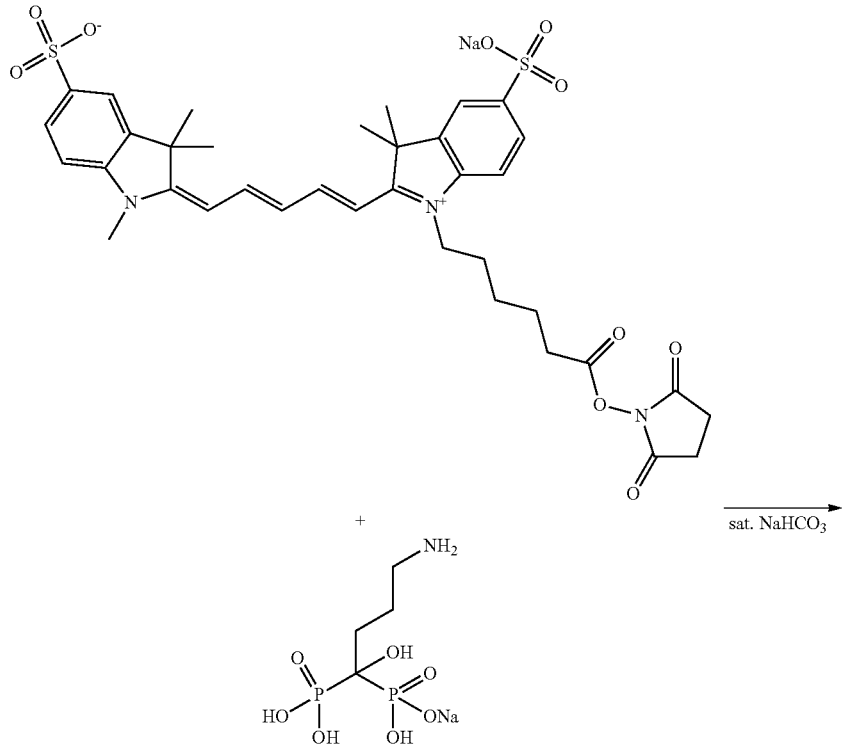

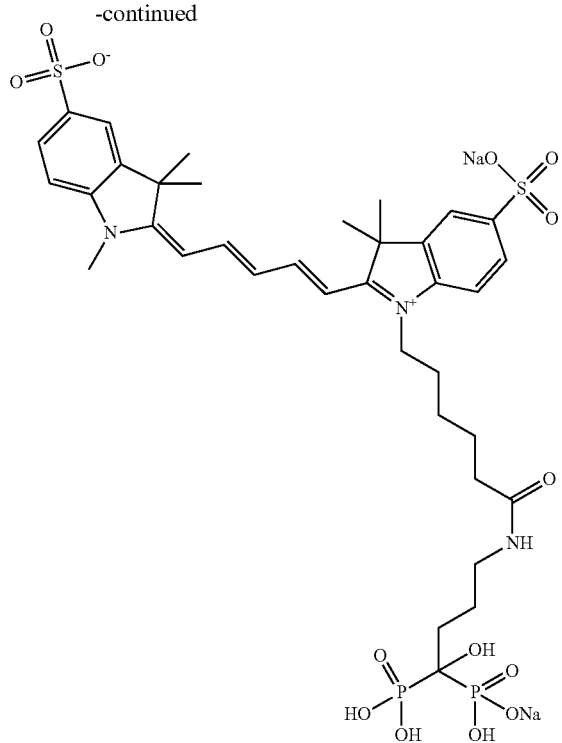

Sodium alendronate (34.0 mg, 125 umol) was dissolved in saturated NaHCO$_{3(aq)}$ (1 mL). Sulfo-Cy5 NHS ester (12.5 mg, 16.4 umol) dissolved in DMF (125 μL) was added and the solution stirred overnight in the dark. The reaction mixture was dialysed (cellulose ester, MWCO 0.1-0.5 kD) with water (4×500 mL with water change at 2 h, 4 h, 6 h and dialysed overnight). The solution was subjected to RP-FCC (Isolera One, SiliaSep™ C18 12 g cartridge) with a gradient from 0 to 100% MeOH in H$_2$O. The fractions were lyophilized to yield Sulfo-Cy5 alendronate (0.94 umol, 6%) as a blue powder.

AS-01-077B (NOT-dronate-Cy5):

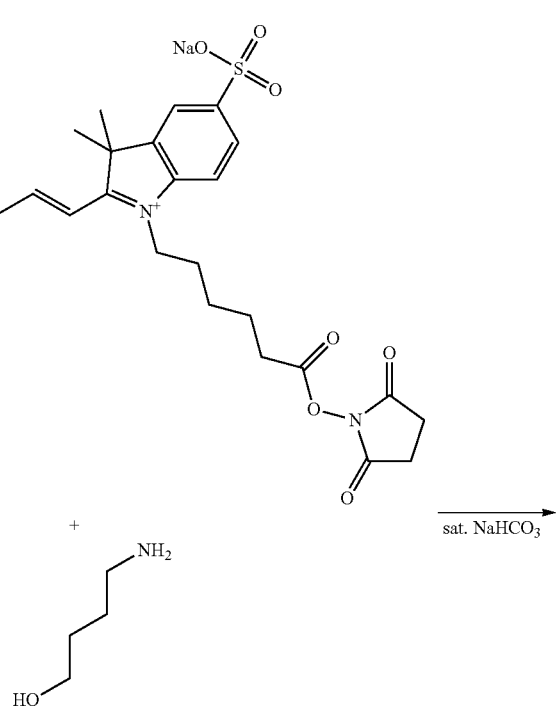

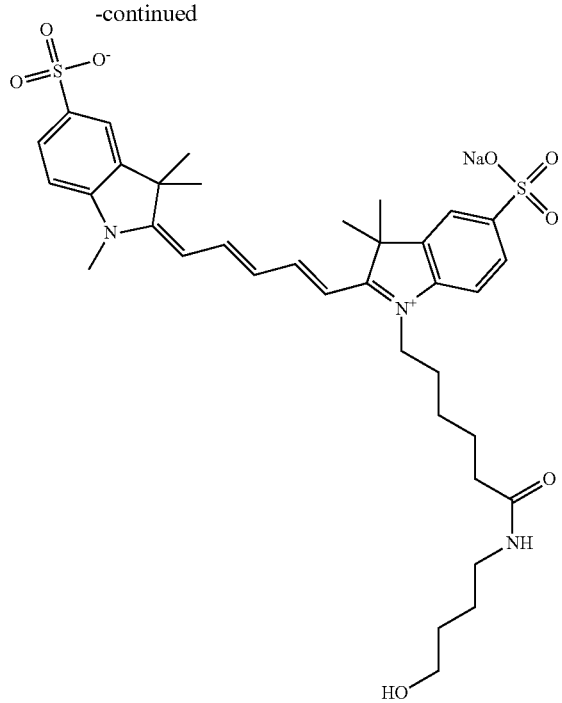

4-Amino-1-butanol (20 mg, 200 umol) was dissolved in saturated NaHCO$_{3(aq)}$ (1 mL). Sulfo-Cy5 NHS ester (12.5 mg, 16.4 umol) dissolved in DMF (125 μL) was added and the solution stirred overnight in the dark. The reaction mixture was dialysed (cellulose ester, MWCO 0.1-0.5 kD) with water (3×500 mL with water change at 2 h, 4 h and dialysed a further 2 h). The solution was subjected to RP-FCC (Isolera One, SiliaSep™ C18 12 g cartridge) with a gradient from 0 to 100% MeOH in H$_2$O. The fractions were lyophilized to yield Sulfo-Cy5 4-amino-1-butanol (1.4 umol, 8%) as a blue powder.

01-051A (Alendronate-FITC):

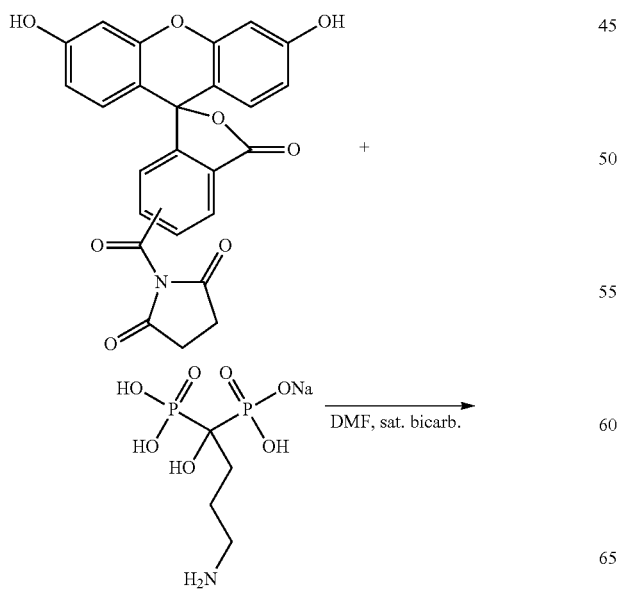

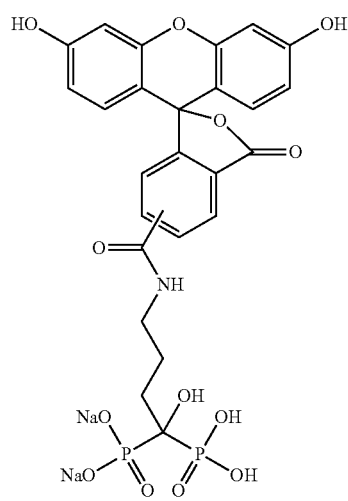

Sodium alendronate (34.0 mg, 106 umol) was dissolved in saturated NaHCO$_{3(aq)}$ (1 mL). Fluorescein (5/6) NHS ester (10 mg, 21 umol) dissolved in DMF (100 μL) was added and the solution stirred for 2 days in the dark. The product was dried, suspended in H$_2$O (1 mL) and dialyzed (cellulose ester, MWCO 0.1-0.5 kD) with water (3×500 mL). The final product's concentration was determined by the UV absorption (8493 nm=70,000 M-1 cm-1). The solution was lyophilized to yield FITC alendronate (8.6 umol, 41%) as an orange powder.

01-051B (NOT-dronate-FITC):

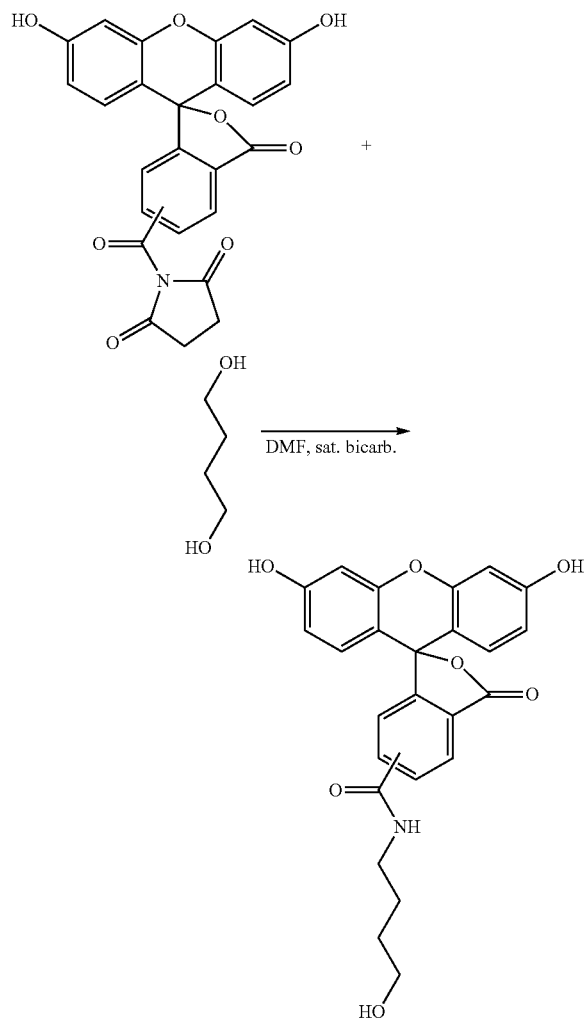

4-Amino-1-butanol (20 mg, 200 umol) was dissolved in saturated NaHCO$_{3(aq)}$ (1 mL). Fluorescein (5/6) NHS ester (10 mg, 21 umol) dissolved in DMF (100 μL) was added and the solution stirred for 2 days in the dark. The reaction mixture was subjected to RP-FCC (0 to 100% MeOH in H$_2$O) and the final product concentration was determined by the UV absorption (8493 nm=70,000 M-1 cm-1). The solution was lyophilized to yield fluorescein-4-butanol (4.8 umol, 23%) as an orange powder.

Sample Preparation:

The following procedure was performed in the dark due to light sensitive reagents. 1 uL of Alendronate-FITC (0.5 mM) and 1 uL of Alendronate-Cy5 (62.5 uM) were added to 20 uL of patient plasma in a microcentrifuge tube. The samples were left to incubate in the dark at room temperature for 30 minutes. After incubation, samples were diluted in 600 uL sterile double-distilled Milli-Q water.

The negative control was prepared by adding 1 uL of 01-051B/NOT-dronate-FITC (0.5 mM) and 1 uL of AS-01-077B/NOT-dronate-Cy5 (62.5 uM) to 20 uL of patient plasma in a microcentrifuge tube. The samples were left to incubate in the dark at room temperature for 30 minutes. After incubation, samples were diluted in 600 uL sterile double-distilled Milli-Q water.

Sample Analysis:

Samples were analyzed using the Apogee A50 Nanoscale Flow Cytometer. Each sample was run in triplicate at a flow rate of 1.39 uL/min for a total of 2 minutes.

Example 1

Quantification of Bone Microparticles in Multiple Myeloma Patient Plasma

Figure 1:
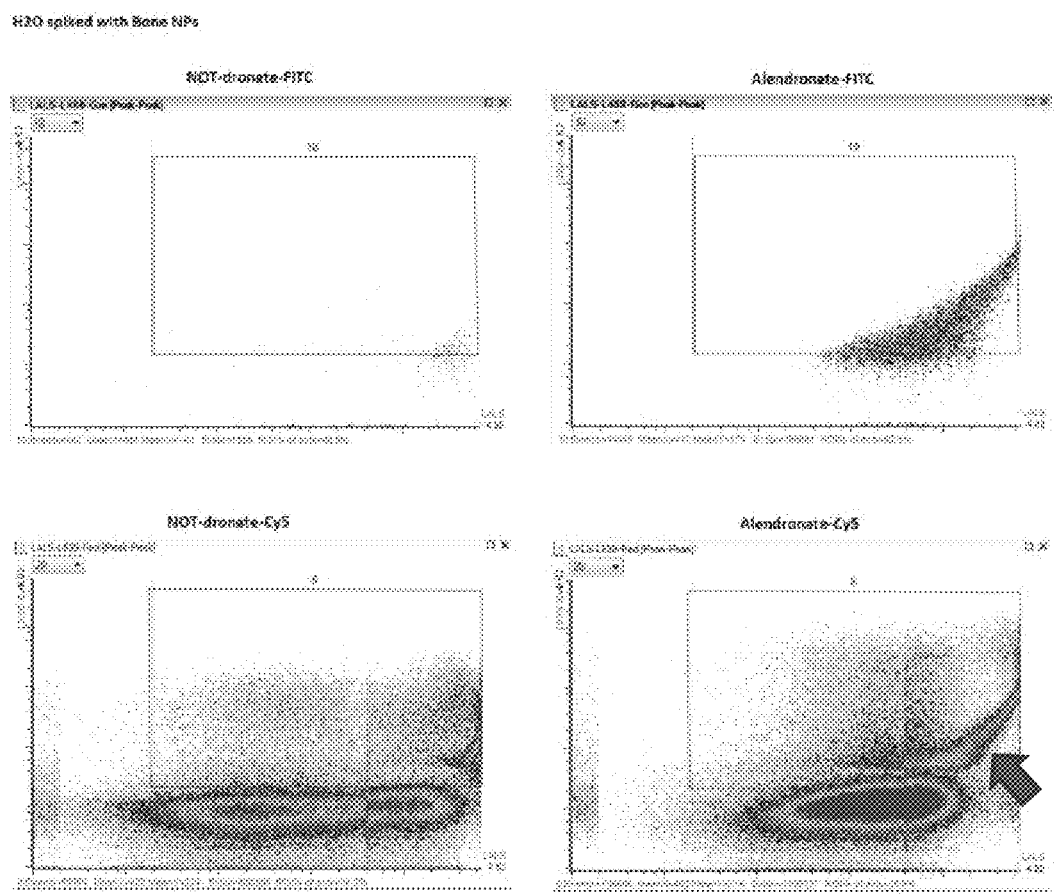
FIG. 1 depicts detection of hydroxyapatite nanoparticles single stained with Alendronate-FITC (AL-FITC) or Alendronate-Cy5 (AL-Cy5) using nanoscale flow cytometry. Bone nanoparticles suspended in phosphate buffered saline (PBS) were incubated with Alendronate-FITC (right top panel) or its negative isotype control, NT-FITC (left top panel). A distinct population was observed to bind AL-FITC (top right panel). When using AL-Cy5, a highly dense population was observed in the red gate (bottom right panel, arrowhead) and a less dense population was observed when stained with NT-Cy5 (bottom left panel). Considerable background was observed in the sample stained with NT-Cy5 (bottom left panel) but was minimal with NT-FITC (top left panel).

The inventors compared the ability of two Alendronate compounds conjugated to FITC or Cy5 to bind to hydroxyapatite nanoparticles that are highly similar in chemical composition to bone and bone fragments hypothesized to be present in subject blood. An isotype negative control was prepared for each Alendronate compound. The isotype negative control for Alendronate-FITC (AL-FITC) was Notdronate-FITC (NT-FITC). The isotype negative control for Alendronate-Cy5 (AL-Cy5) was Notdronate-Cy5 (NT-Cy5). When hydroxyapatite nanoparticles in PBS were labeled with NT-FITC or NT-Cy5, there were minimal and high background levels of NT-positive events respectively (FIG. 1 A, C). When hydroxyapatite nanoparticles were stained with AL-FITC or AL-Cy5, significantly higher AL-positive events were observed (red gate, FIGS. 1B and D) compared to their negative controls (FIG. 1A,C). However, NT-Cy5 produced substantially high levels of background.

Figure 2:
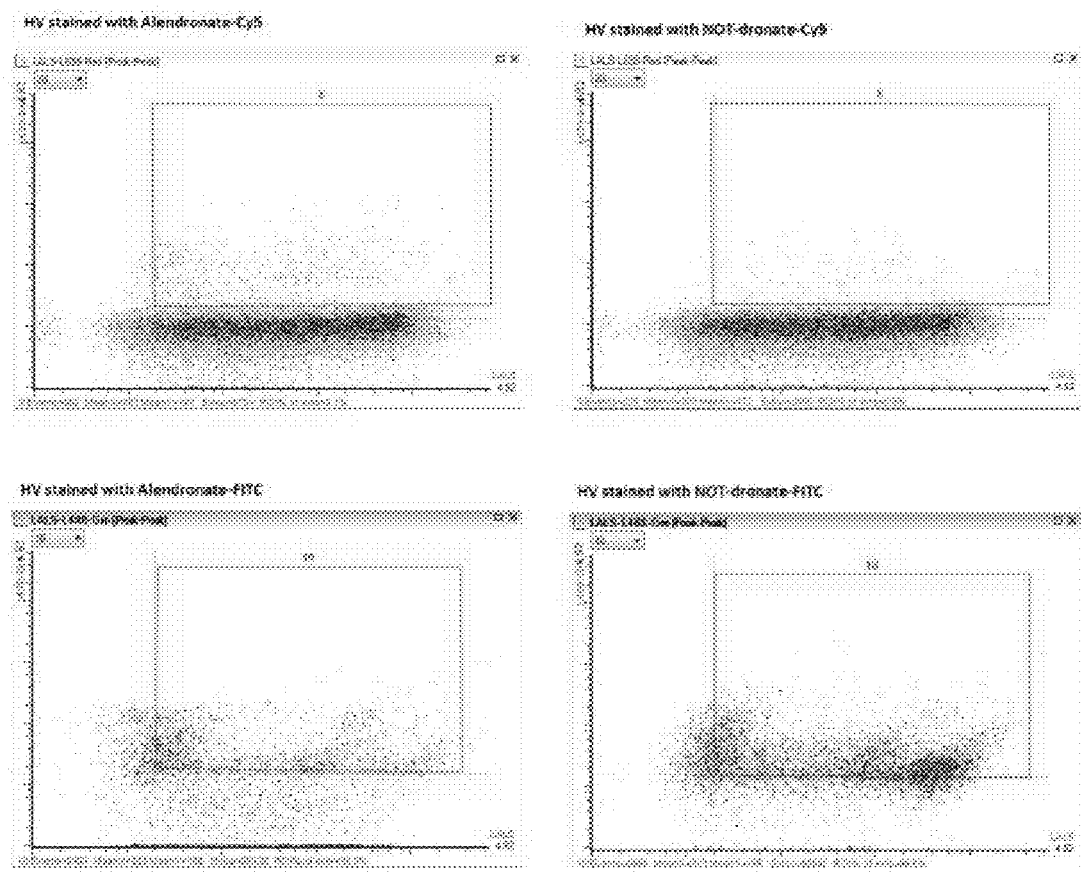
FIG. 2 depicts detection of bone microparticles in healthy volunteer plasma single stained with Alendronate-FITC (AL-FITC) or Alendronate-Cy5 (AL-Cy5) using nanoscale flow cytometry. Plasma from a healthy volunteer (HV) was incubated with AL-Cy5 (right top panel) and its negative isotype control, NT-FITC (left top panel). More events were found in the AL-Cy5 stained sample compared to its isotype negative control NT-Cy5 despite moderate levels of background (top right panel). When using AL-FITC (bottom left panel) and NT-FITC (bottom right panel), a high amount of background was observed in the isotype negative control NT-FITC stained sample.
Figure 3:
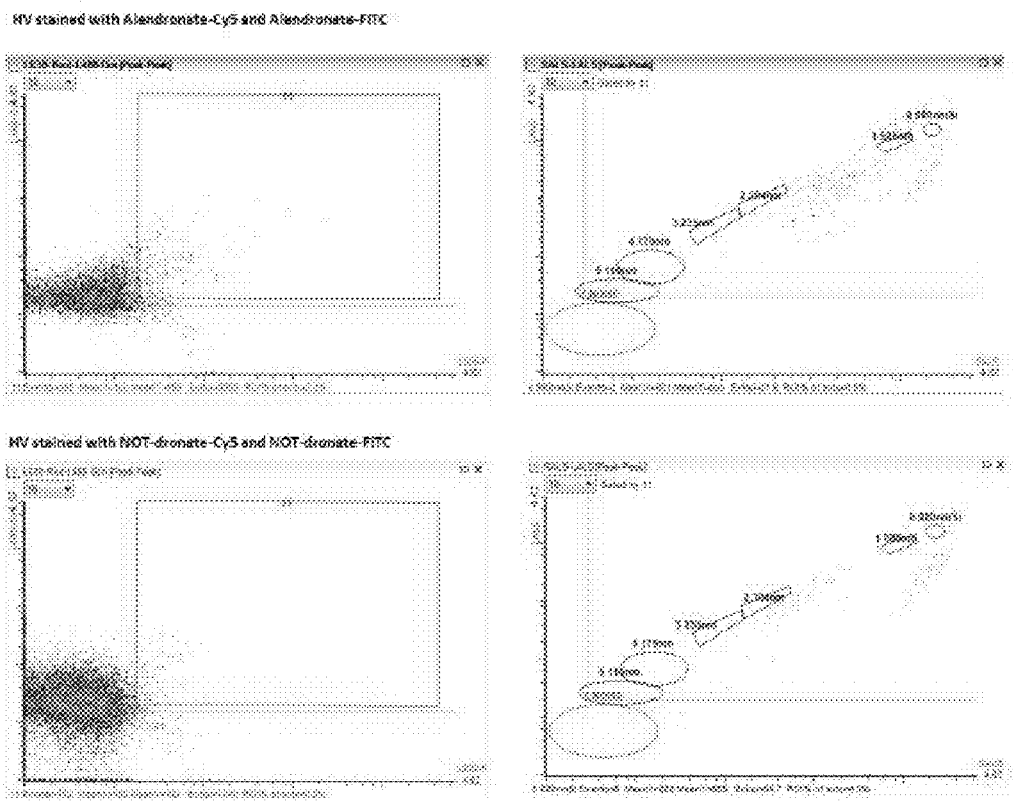
FIG. 3 depicts detection of dual positive AL-FITC and AL-Cy5 bone microparticles in healthy volunteer plasma. Plasma from a healthy volunteer (HV) was incubated with AL-FITC and AL-Cy5 (A, B) or its negative isotype controls, NT-FITC and NT-Cy5 (C, D). More dual-positive events were found in the AL-FITC and AL-Cy5 dual stained sample (A) compared to its isotype negative control (C). Dual positive events exhibit a size distribution of 304 nm-585 nm when events in the red gate of (A) are transposed in a sizing histoplot (B).

Using plasma from a healthy volunteer with no clinical history of bone disease, the inventors found low levels of AL-Cy5 events and even lower levels of NT-Cy5 events (FIGS. 2, A and B). In contrast, low levels of AL-FITC events but significantly higher NT-FITC events (FIG. 2C-D) were found in healthy volunteer plasma. However, when this plasma was dual stained with both compounds and their respective isotype controls, minimal dual positive counts were observed in the isotype control sample (FIG. 3C), whereas a subpopulation of dual-positive events was present in FIG. 3A. When dual positive (AL-Cy5+ve and AL-FITC+ve) events were gated onto a sizing histoplot (FIG. 3B), these putative bone fragments exhibited a size range between 305 nm-585 nm.

Figure 4:
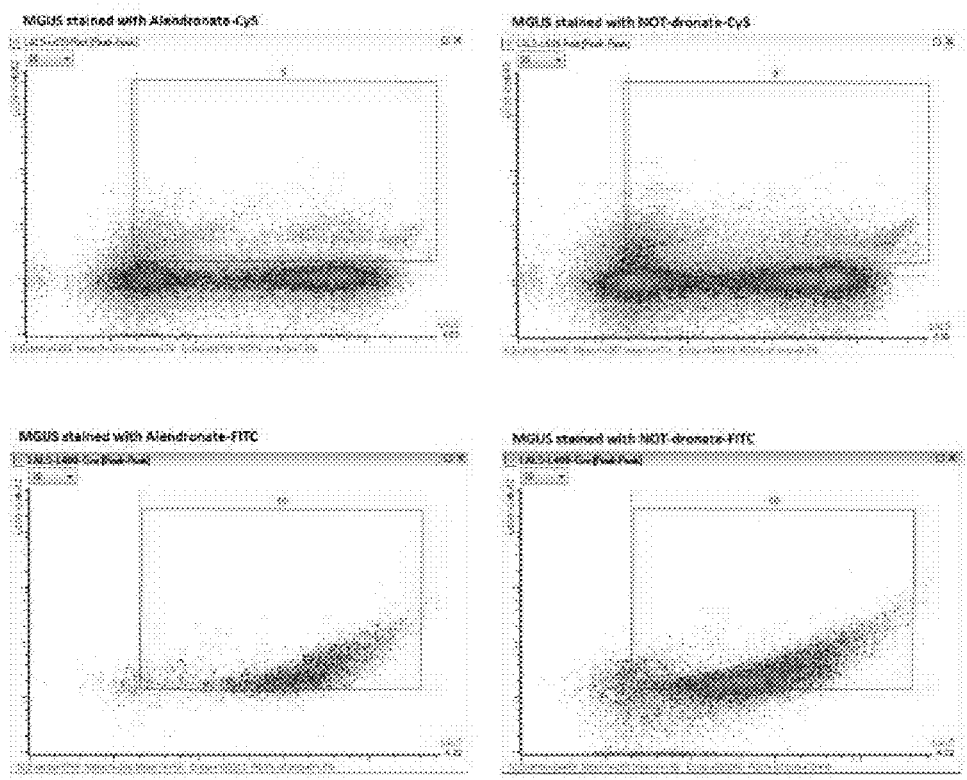
FIG. 4 depicts detection of bone microparticles in plasma from a patient with monoclonal gammopathy of undetermined significance (MGUS) single stained with Alendronate-FITC (AL-FITC) or Alendronate-Cy5 (AL-Cy5). Plasma from a patient with MGUS was incubated with AL-Cy5 (A) or AL-FITC (C) and its negative isotype controls, NT-Cy5 (B) and NT-FITC (D). No difference was observed between AL-Cy5 stained plasma (A) and NT-Cy5 stained plasma because of the high background in (B). When using AL-FITC and NT-FITC, a higher count of events was observed in the NT-FITC negative control stained sample (D) compared to the AL-FITC stained sample (C).
Figure 5:
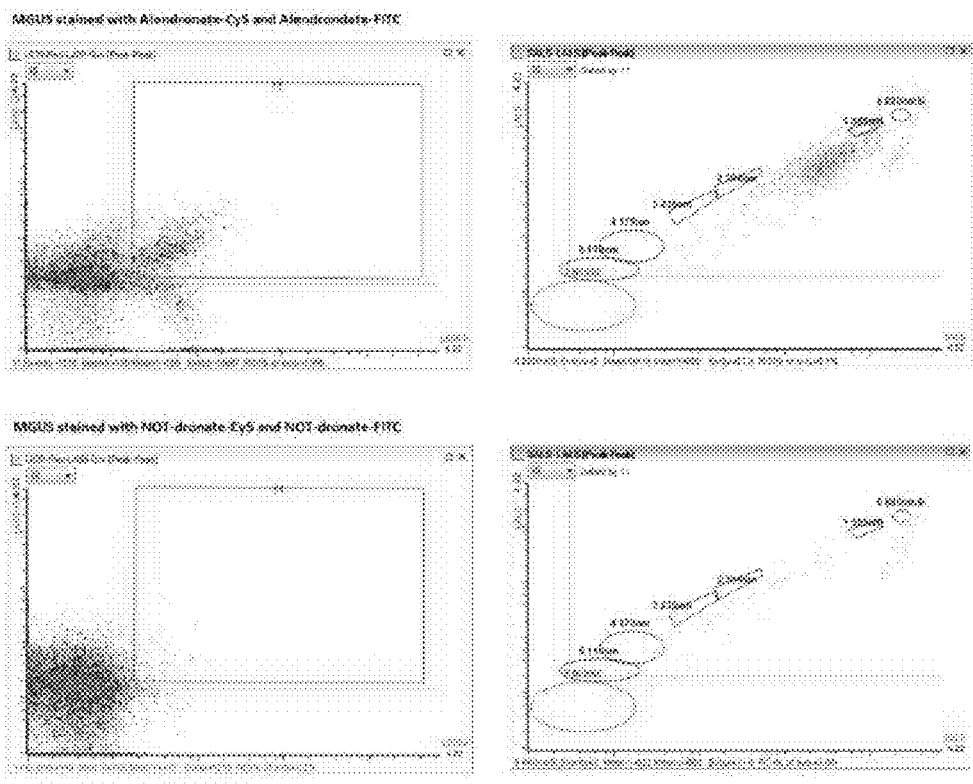
FIG. 5 depicts detection of dual positive AL-FITC and AL-Cy5 bone microparticles in plasma from the patient with MGUS of FIG. 4. Plasma was incubated with AL-FITC and AL-Cy5 (A, B) or its negative isotype controls, NT-FITC and NT-Cy5 (C, D). More dual-positive events were found in the AL-FITC and AL-Cy5 dual stained sample (A)

Using plasma from one patient with Monoclonal Gammopathy of Unknown Significance (MGUS), the inventors found that isotype controls for AL-FITC and AL-Cy5 (FIG. 4A,C) when used alone produced data with high background (FIG. 4B,D). However, when used in combination, a clear dual signal subpopulation was present, suggesting the presence of bone microparticles (FIG. 5A), with minimal background observed in the isotype negative controls (FIG. 5C). When the dual-positive population in FIG. 5A was transposed into a sizing histoplot (FIG. 5B), the bone microparticles exhibited a size range between 400 nm-505 nm. Some MGUS patient plasmas yielded very low dual-positive events (FIG. 7A) and, as expected, single stained plasmas yielded data with high background (FIG. 6D). Therefore, dual-stained events were used to define bone microparticles present in patient plasma.

Plasma from a patient diagnosed with Multiple Myeloma with a positive bone scan was single-stained (FIG. 8) or dual stained (FIG. 9) to quantify bone microparticles. As in the MGUS samples, single stains revealed high background counts in the isotype negative control stains (FIG. 8B,D) and dual staining revealed a distinct subpopulation of dual-positive counts (FIG. 9A) with minimal background in the isotype negative control (FIG. 9C). When these dual-positive events were transposed into a sizing histoplot, bone microparticles exhibiting a size range from 110 nm-880 nm were observed.

A subject's response to disease treatment was analyzed by quantifying bone microparticles in the subject's blood at different time points pre- and post-chemotherapy. In FIG. 10, dual-stained plasmas from a patient undergoing chemotherapy are shown, with the first histoplot (upper panel) revealing the abundance of bone microparticles in the subject's blood prior to chemotherapy. The middle panel represents the bone microparticle profile at 3 weeks post-chemotherapy, a loss in bone microparticle populations as marked by the arrowhead. At 6 weeks post-chemotherapy, an absence of bone microparticles was observed. This set of longitudinally collected data would indicate that a loss of bone microparticles in plasma correlated with the administration of chemotherapy intended to halt osteolytic disease.

Absolute counts of bone microparticles (AL-FITC+AL-Cy5+) in patient plasma from three cohorts were plotted (FIG. 11): healthy volunteer, Multiple Myeloma, and MGUS. Significantly higher bone microparticle counts were observed in multiple myeloma patients and patients with MGUS. Plasma from healthy volunteers generally had lower bone microparticle counts but a subpopulation had moderately high levels of bone microparticles.

The method provided herein defines a bone microparticle event in patient plasma as being less than 1 um in diameter. Such events bind a significant amount of AL-Cy5 and AL-FITC when compared to the same plasma sample analyzed with NT-Cy5 and NT-FITC. When analyzed by the A50-Micro Flow Cytometer, bone microparticle counts per μL of patient plasma were determined. It is contemplated that the method provided herein is also useful for analyzing bone microparticle counts over time, response to chemotherapy or response to other treatments. The method is non-invasive, highly sensitive and amenable to a blood-based format. Absolute counts of bone microparticles can be used to distinguish patients with active bone disease, such as patients with Multiple Myeloma, as well as to identify patients that were initially diagnosed with MGUS that have active bone disease.

Although the invention has been described with reference to certain specific embodiments, various modifications thereof will be apparent to those skilled in the art without departing from the purpose and scope of the invention as outlined in the claims appended hereto.

Any examples provided herein are included solely for the purpose of illustrating the invention and are not intended to limit the invention in any way. Any drawings provided herein are solely for the purpose of illustrating various aspects of the invention and are not intended to be drawn to scale or to limit the invention in any way. The disclosures of all prior art recited herein are incorporated herein by reference in their entirety.

We claim:

1. A method of detecting bone loss in a subject, the method comprising:
    a) obtaining a blood sample from the subject and contacting an aliquot of the blood sample with at least one labeled probe that specifically binds to hydroxyapatite, wherein the at least one labeled probe is Alendronate conjugated with a detectable label;
    b) contacting an aliquot of the blood sample obtained from the subject with an isotype negative control of the at least on labeled probe, wherein the isotype negative control has the formula (I)

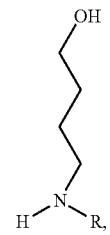

wherein R is a detectable label;
    c) measuring the concentration of hydroxyapatite in the sample by comparing the measured amount of hydroxyapatite bound to the at least one labeled probe with the measured amount of hydroxyapatite bound to the isotype negative control;
    d) calculating the concentration of bone microparticles in the sample based on the measured concentration of hydroxyapatite;
    e) comparing the calculated concentration of bone microparticles with a reference value, wherein the reference value is: (i) the concentration of bone microparticles in blood sample from a healthy subject; or (ii) the concentration of bone microparticles in a prior blood sample obtained from the subject at a time prior to the blood sample obtained in step (a);
    wherein a higher concentration of bone microparticles in the sample compared to the reference value is indicative of bone loss in the subject.

2. The method of claim 1, wherein the step of measuring the amount of hydroxyapatite bound to the at least one labeled probe is conducted using flow cytometry.

3. The method of claim 1, wherein, where bone loss is detected in the subject, the method further comprises treating the subject for the bone loss.

4. The method of claim 1, wherein the subject has or is suspected of having cancer or osteoporosis.

5. The method of claim 1, wherein the detectable label is a fluorophore.

6. The method of claim 5, wherein the fluorophore is FITC or Cy5.

7. The method of claim 1, wherein the method involves monitoring the subject for bone loss over a period of time.

8. The method of claim 1, wherein the subject is undergoing preventive therapy for bone loss and the method involves detecting bone loss in the subject over a period of time to monitor the efficacy of the preventive therapy for bone loss.

* * * * *